(12) United States Patent
McMichael

(10) Patent No.: US 8,367,610 B2
(45) Date of Patent: Feb. 5, 2013

(54) METHOD OF TREATING CRAVINGS BY ADMINISTRATION OF NERVE GROWTH FACTOR

(75) Inventor: John McMichael, Delanson, NY (US)

(73) Assignee: Beech Tree Labs, Inc., Delanson, NY (US)

( * ) Notice: Subject to any disclaimer, the term of this patent is extended or adjusted under 35 U.S.C. 154(b) by 398 days.

(21) Appl. No.: 12/573,706

(22) Filed: Oct. 5, 2009

(65) Prior Publication Data

US 2010/0093631 A1    Apr. 15, 2010

Related U.S. Application Data

(63) Continuation-in-part of application No. 11/767,992, filed on Jun. 25, 2007, now abandoned, which is a continuation-in-part of application No. 10/624,328, filed on Jul. 22, 2003, now abandoned.

(60) Provisional application No. 60/424,443, filed on Nov. 7, 2002.

(51) Int. Cl.
*A61K 38/18* (2006.01)

(52) U.S. Cl. ........ 514/8.4; 514/6.8; 514/18.1; 514/18.4; 514/17.7

(58) Field of Classification Search .................. None
See application file for complete search history.

(56) References Cited

U.S. PATENT DOCUMENTS

| | | | |
|---|---|---|---|
| 5,157,924 A | 10/1992 | Sudmanns et al. | |
| 5,599,560 A | 2/1997 | Siuciak | |
| 6,024,734 A | 2/2000 | Brewitt | |
| 6,090,781 A * | 7/2000 | DeYoung et al. | 514/8.4 |
| 6,663,899 B2 * | 12/2003 | Cleland et al. | 424/491 |
| 2001/0052137 A1 | 12/2001 | Klein | |
| 2002/0002269 A1 | 1/2002 | Milbrandt et al. | |
| 2002/0028786 A1 | 3/2002 | Frey et al. | |
| 2002/0049422 A1 | 4/2002 | Brewitt | |
| 2003/0072793 A1 | 4/2003 | Frey et al. | |

OTHER PUBLICATIONS

Armstrong et al., "Morphologic alterations of choline acetyltransferase-positive neurons in the basal forebrain of aged behaviorally characterized fisher 344 rats," *Neurobiol. Aging*, 14:457-470 (1993).
Beers et al., The Merck Manual of Diagnosis and Therapy, 17th edition, pp. 1525-1539 and 1932-1933 (1999).
Fischer et al., "Progressive decline in spatial learning and integrity of forebrain cholinergic neurons in rats during aging," *Neurobiol. Aging*, 13:9-23 (1992).
Gnahn et al., "NGF-mediated increase of choline acetyltransferase (ChAT) in the neonatal rat forebrain: evidence for a physiological role of NGF in the brain?" *Dev. Brain Res.*, 9:45-52 (1983).
Kordower et al., "Delivery of trophic factors to the primate brain," *Exp. Neurol.*, 124:21-30 (1993).
Markowska et al., "Human nerve growth factor improves spatial memory in aged but not in young rats," *J. Neurosci.*, 14:4815-4825 (1994).
Scali et al., "Nerve growth gactor increases extracellular acetylcholine levels in the parietal cortex and hippocampus of aged rats and restores object recognition," *Neurosci. Lett.*, 170:117-120 (1994).
Thoenen et al., "Neurotrophic factors," *Science*, 229:238-242 (1985).
International Search Report. PCT/US03/31380, United States Patent Office as International Searching Authority, mailed Mar. 12, 2004.

* cited by examiner

*Primary Examiner* — Robert C Hayes
(74) *Attorney, Agent, or Firm* — Marshall, Gerstein & Borun LLP

(57) ABSTRACT

A method for administering nerve growth factor to treat cravings is provided. Pharmaceutical compositions for the treatment of cravings comprising nerve growth factor are also provided.

6 Claims, No Drawings

METHOD OF TREATING CRAVINGS BY ADMINISTRATION OF NERVE GROWTH FACTOR

RELATED APPLICATIONS

This application is a continuation-in-part of U.S. patent application Ser. No. 11/767,992, which was filed Jun. 25, 2007, which is a continuation-in-part of U.S. patent application Ser. No. 10/624,328, which was filed Jul. 22, 2003, which claims the benefit of priority of U.S. Provisional Patent Application Ser. No. 60/424,443, which was filed Nov. 7, 2002, the disclosures of which are incorporated herein by reference in their entireties.

FIELD OF THE INVENTION

The invention involves methods for the treatment of cravings of various sorts by the administration of nerve growth factor (NGF).

BACKGROUND OF THE INVENTION

The present invention provides methods for treatment of psychological conditions. Such psychological conditions, including major depression, hypomania, cyclothymia, anxiety, bipolar disorder, insomnia and other sleep disorders, hyperactivity, attention deficit disorder, chronic fatigue syndrome, premenstrual syndrome (PMS), premenstrual dysphoric disorder (PMDD), and agoraphobia, take an enormous toll on people's ability to work, maintain relationships, communicate effectively, think properly, perform physical activity, and sense the environment around them.

The most common of these psychological conditions is depression, which ranks first among all causes of disability in the United States and second after heart disease, as a cause of healthy years lost to premature mortality and disability (Regier et al., *Arch Gen Psychiatry* 45:977 (1988). Depression can be divided into several types. Major depression is the most severe form of depression characterized by a severe, persistent depressed mood and loss of interest or pleasure in normal activities accompanied by decreased energy, changes in sleep habits, restless behavior, difficulty concentrating, loss of appetite, feelings of guilt or hopelessness, and in severe cases, psychotic symptoms such as hallucinations, delusions, and even suicidal thoughts. An individual must have a history (greater than 2 weeks) of persistent sad moods, loss of interest or pleasure in activities once enjoyed, and feelings of guilt or hopelessness, restless behavior, difficulty concentrating, and even suicidal thoughts in order to make a diagnosis of major depression. The Beck's Depression Scale Inventory, or other screen tests for depression, can be helpful in diagnosing depression.

Major depression can be treated with medications and/or counseling. Studies have shown that antidepressant drug therapy combined with psychotherapy appears to have better results than either therapy alone (Elkin et al., *Arch Gen. Psychiatry* 46:971 (1989). Medications used include, but are not limited to, tricyclic antidepressants, monoamine oxidase inhibitors, selective serotonin re-uptake inhibitor (SSRIs), and some new antidepressant drugs such as bupropion, reboxetine, trazodone, venlafaxine, and mitrazapine. Antipsychotic medications are needed for patients suffering from more severe forms of psychotic symptoms, such as delusions or hallucinations. Types of psychotherapy that have proven to be particularly effective for treating depression include interpersonal therapy, group therapy, and cognitive/behavioral therapy. Often experimenting with the right combination of these drugs and therapy is required by the treating physician. Unfortunately, up to 30% of patients with major depression do not gain substantial benefit from initial antidepressant treatments. Often, it is recommended that if one drug does not improve the mood of a patient after 4-6 weeks of treatment, the drug should be changed (Potter et al., *N. Eng. J. Med.* 325:633 (1991)). Finally, electroconvulsive therapy (ECT), which is a treatment that causes a central nervous system seizure by means of an electric current, is often reserved as a treatment of last resort, in order to improve the mood of severely depressed or suicidal people who do not respond to other treatments. ECT, however, is accompanied by severe side effects, such as long-lasting memory impairment (Hyman et al., Merks Manual of Medicine, Chapter 13 page 13 (2000)).

Alternative therapeutic methods include the use of herbal products for management of chronic conditions, such as psychiatric disorders, including anxiety and depression. In addition, St. John's Wort (hypericum) has recently gained popularity as an adjunct antidepressant in the United States. The National Institute of Health has recently sponsored a Hypericum Clinical Trial comparing 50 to 150 mg/day of sertraline (Zololoft), 900 to 1800 mg/day of St. John's Wort, and placebo in 300 patients with major depression. The conclusion of the study was St. John's Wort was no more effective for treating major depression of moderate severity than a placebo (NIH News Release, Apr. 9, 2002). Side effects of St. John's Wort are mild and primarily include gastrointestinal symptoms and fatigue. Therefore, there is a need in the art for alternative treatments, which are more effective and are associated with fewer side effects for treating major depression.

A second form of depression is chronic low-grade depression, also known as dysthymia. Dysthymia is present most of the time for a period of two or more years wherein an individual experiences a decrease in his/her overall level of energy, appetite, and sleep, as well as has feelings of low self-esteem and hopelessness. These symptoms cause distress and the individual has difficulty functioning in everyday activities. These symptoms, however, are not as severe as those symptoms experienced in major depression. The cause and maintenance of these symptoms are often due to one of the following problems: loss of a friend, substantial disappointment at work or home, prolonged or chronic illness, and alcohol or drug abuse. People who suffer from dysthymia are at an increased risk for episodes of major depression. This produces a behavioral pattern called "double depression," wherein the individual is mildly depressed most of the time, with periodic symptoms of major depression.

Treatments for mild depressive disorders include improving health habits like acquiring adequate, regular sleep and good nutrition. Also, decreasing the use of alcohol and other drugs and becoming involved in healthy activities such as recreation and creative endeavors will relieve depressed feelings. In cases where a subject is unable to shake these "depressed" feelings within a few weeks, the subject may be suffering from major depression and should contact their physician.

The least severe form of depression is a depressed mood. This is an emotional state dominated by feelings of sadness, gloominess, or emptiness, which may be associated with lack of energy. Depressed moods are usually temporary responses to an unhappy or stressful event. Treatments for such conditions are the same as discussed above in treatments for mild depressive disorders.

Finally, diagnosis of depression is different for the different stages in one's life. Elderly depression is one such example. Elderly patients, who present excessive concerns about bodily aches and pains, fatigue, loss of appetite, and sleeping difficulties, are demonstrating, in reality, secondary affects of depression. Depression in the elderly is infrequently diagnosed and untreated due to the fact many older individuals do not admit to the signs or symptoms of depression. Depression in adolescents also requires careful examination. For example, physical examination is used to rule out other medical causes for depressive symptoms. Careful psychiatric evaluations are required to assess the history of the persistent sad, empty, or irritable state of the adolescent patient, along with obtaining information about whether other family members have a history of depression.

Bipolar Disorders

Bipolar disorder is a chronic disease affecting over 2 million Americans at some point in their lives. Bipolar disorder affects men and women equally and appears between the ages of 15 and 25. As opposed to unipolar major depression, the incidence of biopolar disorder does not vary widely around the world. The exact cause is unknown, but it is linked to areas of the brain which regulate mood, and has a strong genetic component. The American Psychiatric Association's "Diagnostic and Statistical Manual of Mental Disorders" describes two types of biopolar disorder, type I and type II. In type 1 (formerly known as manic depressive disorder), there has been at least one full manic episode. People with this type, however, may also experience episodes of major depression. In type II disorder, periods of "hypomania" involve more attenuate (less severe) manic symptoms that alternate with at least one major depressive episode. When the patients have an acute exacerbation, they may be in a manic state, depressed state, or mixed state. The manic phase is characterized by elevated mood, hyperactivity, over-involvement in activities, inflated self-esteem, a tendency to be easily distracted, and little need for sleep. In the depressive phase, there is loss of self-esteem, withdrawal, sadness, and a risk of suicide. Either the manic or the depressive episodes can predominate and produce a few mood swings, or the patterns of the mood swing may be cyclic. While in either phase, patients may abuse alcohol or other substances, which worsens the symptoms.

Methods for treating bipolar disorders differ depending upon the state of the patient. During an acute phase, hospitalization may be required to control the symptoms. In order to reduce the risk of switching into mania, hypomania or rapid cycling, a combination of a mood stabilizer (e.g. lithium; valproate) and antidepressants (e.g., bupropion) is effective for controlling bipolar disorders. Even though lithium is effective in controlling manic and depressive relapses, careful medical supervision along with maintaining salt intake, avoiding nonsteroidal anti-inflammatory drugs, and undertaking weight-reduction diets are all required in order to reduce possible renal failure. Valproate also is characterized by severe side effects including nausea, vomiting, anorexia, heartburn, and diarrhea. Finally, the use of antidepressants for suppressing bipolar disorder must also be carefully monitored in order to achieve full symptomatic remission. Therefore, safer therapeutic methods are needed in the art in order to reduce the severe side effects associated with current treatments of bipolar disorders.

Cyclothymic disorders are similar to bipolar disorders, but less extreme. Cyclothymic disorders are characterized by stages of mild mood changes with stages of mild depression and excitement (hypomania). The changes in mood are very irregular and abrupt, but the severity of the swings is less. Cyclothymia is treated like biopolar disorders, though often not as aggressively. Thus, safer treatments are needed in the art.

Anxiety Disorders

Anxiety disorders, panic attacks, and agoraphobia are conditions that occur as a manifestation of primary mood disorders such as depression. Anxiety is a feeling of apprehension or fear that lingers due to an individual's perception of persistent and unrelenting stress. Anxiety is accompanied by various physical symptoms including twitching, trembling, muscle tension, headaches, sweating (e.g., night sweats), dry mouth, or difficulty swallowing. Some people also report dizziness, a rapid or irregular heart rate, increased rate of respiration, diarrhea, or frequent need to urinate when they are anxious. Fatigue, irritable mood, sleeping difficulties, decreased concentration, sexual problems, and nightmares are also common. Some people are more sensitive to stress and are thus more likely to develop anxiety disorders. The propensity to succumb to anxiety attacks may be due to genetic predisposition or by previous (e.g. childhood) exposure to certain stresses.

Treatment of anxiety disorders includes diagnostic tests for blood differential and thyroid function as well as an electrocardiogram (EKG). If any worrisome physical signs or symptoms do not accompany the anxiety, a referral to a mental health care professional is recommended. Psychotherapy such as cognitive-behavior therapy (CBT) along with the medication benzodiazepines, which facilitate the actions of γ-aminobutyric acid (GABA), the major inhibitory neurotransmitter in the nervous system, are the most effective in severe cases of anxiety. In addition to these treatments, use of antidepressants such as imipramine and the selective serotonin re-uptake inhibitor (SSRI) paroxetine have been shown to produce antianxiety benefit to anxiety patients (Rocca et al., *Acta Psychiatr Scand* 95:444 (1997)). Treatment with benzodiazepines, however, is accompanied by fatigue, drowsiness, and unsteadiness. After successive treatments with benzodiazepines, patients often develop dependence to the drug and, therefore, careful medical monitoring is required. Thus, there is a need in the art for treatments that provide less drug dependence along with a reduction in side effects and costs.

Panic disorder, one of the anxiety disorders, is characterized by repeated and unexpected attacks of intense fear and anxiety. Panic attacks are usually not related to a particular situation and typically "peak" within ten minutes of their onset. The exact cause of panic disorder is unknown, but it is associated with multiple physiological factors. Panic disorder can occur with or without agoraphobia, but agoraphobia develops in one-third of cases. Agoraphobia is a disorder characterized by avoidance of crowds, and open and public places, particularly if escape or assistance is not immediately available. The development of agoraphobia may involve learned behavior, since it reflects a fear of experiencing panic attacks in unprotected settings, and sometimes the association of panic attacks with areas where they have occurred. The prevalence rate of panic attacks in the population is as high as 1.5 to 5% (Cruz, et al). Panic disorder can occur in children, but the average age of onset is 25 years old. Panic disorder affects middle-aged and older adults as well. Studies have shown that women are 2 to 3 times more likely to be affected (Cruz, et al.).

Symptoms of panic disorder include shortness of breath, dizziness, palpitations, trembling, sweating, choking, nausea, numbness, chest pain, hot flashes or chills, fear of dying, fear of losing control, and fear of going insane. Symptoms of agoraphobia include anxiety about being in places where escape might be difficult, fear of being alone, fear of losing control in a public place, feeling of helplessness, and feelings of detachment. Treatments for both disorders are similar to treatment of anxiety. Antidepressant medicines are effective for treatment of many people with panic disorder and agoraphobia including SSRIs such as Paxil. Behavior therapies are also used in conjunction with drug therapy including relaxation techniques, pleasant mental imagery, and cognitive behavioral therapy to restructure distorted and harmful interpretations of particular situations. As discussed above, the disadvantage of these therapies is possible drug dependence, harmful side effects, and costs. Therefore, there is a need in the art to develop novel methods for treating panic disorders and agoraphobia.

Premenstrual Syndrome (PMS)

Woman's physical, emotional, and behavioral changes associated with phases of their menstrual cycle may worsen mental disorders such as depression and bipolar disorder (discussed below). These changes are referred to as premenstrual syndrome (PMS). In some women, these changes occur regularly, are sometimes severe, and are characterized as feelings of depression, irritability, and other emotional and physical changes. These changes typically begin after ovulation and become gradually worse until menstruation starts. PMS is estimated to affect 70% to 90% of women during their childbearing years. Thirty to forty percent of women suffer from PMS symptoms severe enough to interfere with daily living activities. Wide ranges of physical and emotional symptoms are associated with PMS. By definition, such symptoms must occur during the second half of the menstrual cycle (14 days or more after the first day of the menstrual cycle) and be absent for about 7 days after a menstrual period ends. Symptoms of PMS include, but are not limited to the following: headache, swelling of ankles, feet, and hands, backache, abdominal cramps, breast tenderness, weight gain, bloating, anxiety, confusion, depression, forgetfulness, irritability, fatigue, low self-esteem, and paranoia.

Current treatments for PMS include self-care methods such as exercise and dietary measures wherein nutritional supplements such as vitamin B6, calcium, and magnesium are used. In addition, prostaglandin inhibitors may be prescribed for women with significant pain including headache, backache, menstrual cramping, and breast tenderness. Diuretics can be prescribed for women found to have significant weight due to fluid retention. Psychiatric medications and/or therapy may be used for women who exhibit a moderate to severe degree of anxiety, irritability, or depression. Finally, oral contraceptives may decrease PMS symptoms. Although these treatments provide relief to most women, more effective treatments that eliminate or reduce side effects and costs are still needed in the art.

Premenstrual Dysphoric Disorder (PMDD)

An estimated 3-4% of women suffer severe premenstrual mood symptoms that significantly interfere with work and social functioning. These severe premenstrual symptoms are diagnosed as premenstrual dysphoric disorder (PMDD) or mid-cycle dysphoria. The occurrence of PMDD is higher in women in their late 20s and early 40s, those with at least one child, those with a family history of major depression disorder, or women with a past medical history of either postpartum depression or an affective mood disorder. PMDD differs from PMS in that prospective premenstrual mood symptoms described above occur across multiple menstrual cycles rather than the latter half of the menstrual cycle. Adequate diagnosis is important, because PMDD symptoms may be severe enough to prevent women from maintaining normal function. These symptoms, combined with a patient already suffering from depression, place these patients at a significantly higher risk of committing suicide during the latter half of their menstrual cycle.

Treatments for PMDD include hormone agonist therapy (gonadotropin-releasing hormone (GNRH) agonist leuprolide), and serotoninergic antidepressant therapy (clomipramine, fluoxetine, sertraline, and citalopram). These therapies have demonstrated efficacy in controlling PMDD, but require continuous pharmacotherapy throughout the menstrual cycle, which increases the side effects and costs of these treatments. Intermittent treatments of PMDD with medication administered daily only during the luteal phase (e.g. for 14 days premenstrually) is being studied, but at present has not been implemented. Thus, there is a need in the art for a therapeutic method for treating PMDD and PMS wherein the side effects and costs are reduced and continuous pharmacotherapy is not required.

Other Psychological Disorders

Attention Deficit Disorder (ADD) is the most commonly diagnosed psychological disorder of childhood, affecting 3% to 5% of school aged children. Symptoms include developmentally inappropriate levels of attention, concentration, activity, distractibility, and impulsivity. There are three sub-categories of attention deficit disorder: (1) attention deficit/hyperactivity disorder of the combined type; (2) attention deficit/hyperactivity disorder of the predominantly inattentive type; and (3) attention deficit/hyperactivity disorder of the predominantly hyperactive or impulsive type. Despite much progress in the diagnosis and treatment of ADD, the treatment for this disorder remains highly controversial. While the cause of attention deficit disorder is unknown, scientists have determined a neurological basis for the disease and genes have been identified that are thought to be involved in ADD.

The most effective treatment strategy for ADD is using psychotropic medications such as Dexedine (dextroamphetamine), Ritalin (methylphenidate), and Cylert (magnesium pemoline). Antidepressants (such as amitriptyline or fluoxetine), tranquilizers (such as thioridazine), alpha-adrenergic agonist (clonidine), and caffeine have also been tried to treat ADD. The disadvantage of these drugs is the lack of long term information on the affect these drugs have on the cognitive and emotional development of ADD children. In addition, medications such as antidepressants, tranquilizers, and caffeine have met with little success. A significant amount of research has been carried out studying psychological therapeutic treatments such as contingency management (e.g. time out), cognitive-behavioral treatment (e.g. self monitoring, verbal self instruction, problem solving strategies, and self reinforcement), parent counseling, and individual psychotherapy. Studies using these techniques have yielded mixed results and no studies have been carried out combining psychological interventions with stimulant medications. Therefore, parents are directed to manage the symptoms and direct the child's energy to constructive and educational paths.

Exacerbations of Depression or Other Psychological Conditions

If untreated, depression or other psychological conditions can lead to further complications over a period of time directly dependent upon the severity of depression or psychological condition. There is usually an increased risk of problems with physical and emotional health, which can lead to premature death due to an accentuated medical illness. In turn, physical and emotional maladies such as chronic fatigue syndrome, constipation, tension headaches, and various sleep disorders perpetuate the depressive state of an individual (along with anxiety and bipolar disorders). Depression also increases the risk of tobacco dependence and/or alcohol abuse and/or drug-related problems. Finally, risk of committing suicide is increased up to as much as 15% of those people who suffer from depressive disorders such as major depression. Therefore, there is a need in the art for more improved treatments of depression, which will lead to improvement of other physical, emotional, and substance abuse maladies and vice versa.

Sleep Disorders

Another secondary effect of depression and other psychological conditions is sleep disorders. A sleep disorder is a disruptive pattern of sleep that may include difficulty falling or staying asleep, falling asleep at inappropriate times, excessive total sleep time, or abnormal behaviors associated with sleep. There are more than 100 different disorders of sleeping and waking. They can be grouped into four main categories: problems with staying and falling asleep (insomnia, e.g.), problems with staying awake (sleep state misperception, e.g.), problems with adhering to a regular sleep schedule (hypersomnias such as narcolepsy, e.g.), and sleep disruptive behaviors (sleep walking, e.g.). Both insomnia and sleep disruptive behaviors could be direct results of a patient suffering from a psychological disorder such as depression or anxiety.

Insomnia includes any combination of difficulty with falling asleep, staying asleep, intermittent wakefulness, and early-morning awakening and can lead to the following disorders: psychophysiological, delayed sleep phase syndrome, hypnotic dependent disorder, and stimulant dependent sleep disorder. Episodes may be either transient (2-3 weeks) or chronic. Common factors associated with insomnia are depression, anxiety, stress, illness, caffeine, abuse of alcohol, medication, illness, physical discomfort, and counterproductive sleep habits such as early bedtimes and daytime napping. Treatment of insomnia is related to the cause. If there is an obvious physical or psychological cause (such as depression), it is the first focus of treatment.

Sleep disruptive behaviors include sleep terror disorder, sleep walking or REM behavior disorders (a type of psychosis related to lack of REM sleep and lack of dreaming). Symptoms of sleep disruptive behaviors are depressed mood, anxiety, apathy, difficulty concentrating, irritability, daytime fatigue, drowsiness, and difficulty falling asleep. Again, treatment of sleep disruptive behaviors is often related to the cause. If there is an obvious physical or psychological cause, it is the first focus of treatment.

Tension Headaches

A tension headache is one of the most common forms of headache. It can occur at any age, but is most common in adults and adolescents. If headaches occur two or more times weekly for several months or longer, the condition is considered chronic. Tension headache is a result of contraction of the neck and scalp muscles. One cause of this muscle contraction is a response to stress, depression, or anxiety. Any activity that causes the head to be held in one position can cause a headache. Other causes include eye-strain, fatigue, alcohol use, excessive smoking, excessive caffeine use, or conditions such as sinus infection, nasal congestion, overexertion, colds, influenza, etc. Tension headaches are not associated with structural lesions in the brain. Current treatment is aimed at relieving symptoms and preventing reoccurrence of the headache. Stress management is one such treatment aimed at removal and control of precipitating factors such as anxiety or depression. There is a need, however, in the art for more effective treatments for tension headaches.

Chronic Fatigue Syndrome

Chronic fatigue syndrome is a condition of prolonged and severe tiredness and weakness (fatigue) that is not relieved by rest and is not directly caused by other conditions. Recent studies have shown that chronic fatigue syndrome may be caused by inflammation of pathways in the nervous system; and that this inflammation may be some sort of immune response or autoimmune process. Chronic fatigue syndrome may occur when a viral illness is complicated by an inadequate or dysfunctional immune response. Other factors such as age, prior illness, stress, environment or genetic disposition and depression may also play a role in the disease. Although depression is indirectly related to chronic fatigue syndrome, it may contribute to the unusual nervous system symptoms associated with this disease. Many people with chronic fatigue syndrome experience depression and other psychological problems that may improve upon treatment. There is no current treatment that has proven to be effective in curing chronic fatigue syndrome. Some proposed treatments are antiviral drugs, medications to treat depression, medications to treat anxiety, and medications to treat pain, discomfort, and fever. Even though depression and anxiety may not be directly linked to chronic fatigue syndrome, depression and other psychological disorders are intricately interrelated with this disease and, therefore, there is a need in the art to find new innovative ways for treating these diseases.

Constipation

Constipation is a relative term. When the stool is hard, infrequent, and requires significant effort to pass, the person has constipation. Constipation may cause discomfort with passage of stools, and passage of large, wide stools may tear the mucosal membrane of the anus, especially in children, causing bleeding and the possibility of an anal fissure. Constipation can be caused by changes in diet, decrease in physical activity, diseases of the bowel, congenital diseases, medications, dehydration, behavior and psychological problems such as depression and anxiety, and neurological diseases. Depression and anxiety are again aggravating factors that contribute to a person suffering from constipation. There is a need in the art to focus on treatment of the depression or anxiety disorder in order to overcome the secondary effects of conditions like constipation.

A patient is considered to have chronic (long duration) constipation if (1) for at least 12 months, patients not taking laxatives report two or more of the following: fewer than three bowel movements per week; excessive straining during at least 25% of bowel movements; passage of hard or pelletlike stool during at least 25% of bowel movements; a feeling of incomplete evacuation for at least 25% of bowel movements; or (2) for at least 12 months, patients have an average of fewer than two bowel movements per week.

Cravings

Substance-related disorders appear to be caused not by a single agent but by a combination of social, biological, and psychological factors. Stress can serve as an inducement for craving or addictive behavior, especially chronic stress, and with continued or repeated use of the substance in question, a dependency of physiological and/or psychological origin. Simple habituation can be complicated by a growing dependency, especially if the substance craved provides a sense of happiness or pleasure via the dopamine or other pathway. Often depression is thought to be a prelude to craving or dependence, although it has likewise been argues that craving leads to depression.

Regardless of origin, craving reflects a biochemical process which, in theory, if interrupted could lead to correction of the malady by regulating those bio-active molecules associated with addiction pathways in such a manner as to restore relative homeostasis at a molecular, or sub-molecular level. Accordingly, there remains a desire for methods and compositions for the treatment of cravings.

Nerve Growth Factor

Nerve growth factor (NGF), a prototypical neurotrophic factor and member of the neurotrophin family, promotes a wide range of responses in target cells. These responses include, but are not limited to, neuron differentiation, maintenance of neuronal survival, and regulation of metabolic activities. Nerve growth factor is well-characterized neurotrophic factor that is essential for the normal development and function of basal forebrain cholinergic neurons in the central nervous system (CNS) (Ghahn et al., 1983; Thoenen and Edgar, 1985). A central area of research in application of nerve growth factor has been its application to age-related cognitive impairments due to the atrophy or loss of basal forebrain cholinergic neurons (Armstrong et al., Neurobiol. Aging 14:457-470 (1993)). For example, studies have shown the intraventricular infusion of NGF can reduce cholinergic neuron atrophy and improve spatial learning or memory retention in aged rats (Scali et al., Neurosci Lett 170:117-120 (1994); Markowska et al., J. Neurosci 14:4815-4825 (1994)). Due to studies indicating decreased immunoreactivity for the NGF receptor in basal forebrain of aged rodents, neural growth factor appears to be linked to spatial learning and memory retention (Fischer et al., Neurobiol. Aging 13:9-23 (1992)). One example of therapeutic uses of NGF includes administering NGF to patients with senile dementia of the Alzheimer's type (SDAT). The problem of such treatment is NGF does not pass through the blood-brain barrier in physiologically relevant amounts and treatments required intracranial surgery (Kordower et al., Exp. Neurol. 124:21-30 (1993). Novel carrier systems consisting of NGF covalently linked to an anti-transferrin receptor antibody (OX-26) have been able to cross the blood-brain barrier.

Despite these recent applications of nerve growth factor, there remains a desire to use NGF to remedy other neurological disorders. Moreover, there exists a growing concern over the widespread use of psychotropic drugs for treating disorders such as depression, anxiety, bipolar disorder. Accordingly, there remains a desire in the art for improved treatment of various psychological conditions by administration of safer compounds that are relatively inexpensive, safe without accompanying side effects, and that can easily be administered.

SUMMARY OF THE INVENTION

The present invention provides methods for treating psychological conditions by administering nerve growth factor. Specifically, the invention provides methods for alleviating symptoms of a psychological condition such as depression, bi-polar disorders, anxiety disorders, panic attacks, agoraphobia, attention deficit syndrome, and mid-cycle dysphoria by administering to a patient in need thereof, nerve growth factor in an amount effective to treat one or more symptoms of the psychological condition.

Methods of the invention comprise administration to a patient suffering from a psychological condition such as depression, bi-polar disorders, anxiety disorders, panic attacks, agoraphobia, attention deficit syndrome, mid-cycle dysphoria, premenstrual dysphoric disorder (PMDD), and premenstrual syndrome (PMS) an effective amount of nerve growth factor. The nerve growth factor is preferably administered in an amount ranging from about 0.001 to 10 microgram per day and is preferably formulated in a liquid vehicle and provided at a concentration of approximately 0.04 micrograms as a single drop. A single drop of nerve growth factor is within the range of 0.001 to 1 microgram. More preferably, a drop of nerve growth factor composition is in the amount of 0.02 micrograms per drop. The nerve growth factor composition is more preferably administered in an amount ranging from about 0.05 to 1 microgram per day or even more preferably administered in an amount ranging from about 0.01 to 0.1 micrograms per day. A preferred route of administration is sublingual, but other routes, such as bucal, oral drench, subcutaneous, intradermal, and intravenous, are expected to work.

The invention also provides a method of alleviating symptoms of a psychological condition selected from the group consisting of sleep disorders, chronic fatigue syndrome, tension headaches, and the physical discomfort of constipation that arise as a result of complications from a psychological condition by administering nerve growth factor to a patient in need thereof, wherein the nerve growth factor is in an amount ranging from 0.001 to 10 micrograms per day, and is preferably formulated in a liquid vehicle and provided at a concentration of approximately 0.04 micrograms as a single drop. A single drop of nerve growth factor is within the range of 0.001 to 1 microgram. More preferably, a drop of nerve growth factor composition is in the amount of 0.02 micrograms per drop. The nerve growth factor composition is more preferably administered in an amount ranging from about 0.05 to 1 microgram per day or even more preferably administered in an amount ranging from about 0.01 to 0.1 micrograms per day. A preferred route of administration is sublingual, but other routes, such as bucal, oral drench, subcutaneous, intradermal, and intravenous are expected to work.

The invention also provides pharmaceutical compositions and methods for alleviating cravings including those associated with addiction including cravings for sugars, carbohydrates, alcohol, nicotine, cocaine, amphetamine, opiate and non-opiate analgesics other prescription drugs and the like by administration of an effective amount of nerve growth factor (NGF) or a subunit thereof. Particularly preferred is the use of the beta-subunit of NGF. The nerve growth factor is preferably administered in an amount ranging from about 0.001 to 10 microgram per day and is preferably formulated in a liquid vehicle and provided at a concentration of approximately 0.04 micrograms as a single drop. A single drop of nerve growth factor is within the range of 0.001 to 1 microgram. More preferably, a drop of nerve growth factor composition is in the amount of 0.02 micrograms per drop. The nerve growth factor composition is more preferably administered in an amount ranging from about 0.05 to 1 microgram per day or even more preferably administered in an amount ranging from about 0.01 to 0.1 micrograms per day. A preferred route of administration is sublingual, but other routes, such as bucal, oral drench, subcutaneous, intradermal, and intravenous, are expected to work.

The invention also provides a pharmaceutical composition for administering to a subject or patient for alleviating symptoms of a psychological condition selected from the group consisting of depression, bi-polar disorders, anxiety disorders, panic attacks, agoraphobia, attention deficit syndrome, premenstrual syndrome (PMS), premenstrual dysphoric disorder (PMDD), mid-cycle dysphoria and cravings wherein the nerve growth factor is in an amount effective to treat one or more symptoms of said psychological condition. In one aspect, the composition further comprises a pharmaceutically acceptable carrier, excipient or diluent. The nerve growth factor composition is preferably administered in a dosage amount ranging from about 0.001 to 10 micrograms per day, and is preferably formulated in a liquid vehicle and provided at a concentration of approximately 0.04 micrograms as a single drop. A single drop of nerve growth factor is within the range of 0.001 to 1 microgram. More preferably, a drop of nerve growth factor composition is in the amount of 0.02 micrograms per drop. The nerve growth factor composition is more preferably administered in an amount ranging from about 0.05 to 1 microgram per day or even more preferably administered in an amount ranging from about 0.01 to 0.1 micrograms per day. A preferred route of administrating the composition is sublingual, but other routes, such as bucal, oral drench, subcutaneous, intradermal, and intravenous are expected to work.

The invention also provides methods comprising administration to a patient suffering from constipation an effective amount of nerve growth factor. In one aspect, the constipation is chronic constipation. The nerve growth factor is preferably administered in an amount ranging from about 0.001 to 10 microgram per day and is preferably formulated in a liquid vehicle and provided at a concentration of approximately 0.04 micrograms as a single drop. A single drop of nerve growth factor is within the range of 0.001 to 1 microgram. More preferably, a drop of nerve growth factor composition is in the amount of 0.02 micrograms per drop. The nerve growth factor composition is more preferably administered in an amount ranging from about 0.05 to 1 microgram per day or even more preferably administered in an amount ranging from about 0.01 to 0.1 micrograms per day. A preferred route of administration is sublingual, but other routes, such as bucal, oral drench, subcutaneous, intradermal, and intravenous, are expected to work.

The invention also provides a pharmaceutical composition for administering to a subject or patient for treating constipation wherein the nerve growth factor is in an amount effective to treat said constipation. In one aspect, the constipation is chronic constipation. In one aspect, the composition further comprises a pharmaceutically acceptable carrier, excipient or diluent. The nerve growth factor composition is preferably administered in a dosage amount ranging from about 0.001 to 10 micrograms per day, and is preferably formulated in a liquid vehicle and provided at a concentration of approximately 0.04 micrograms as a single drop. A single drop of nerve growth factor is within the range of 0.001 to 1 microgram. More preferably, a drop of nerve growth factor composition is in the amount of 0.02 micrograms per drop. The nerve growth factor composition is more preferably administered in an amount ranging from about 0.05 to 1 microgram per day or even more preferably administered in an amount ranging from about 0.01 to 0.1 micrograms per day. A preferred route of administrating the composition is sublingual, but other routes, such as bucal, oral drench, subcutaneous, intradermal, and intravenous are expected to work.

DETAILED DESCRIPTION OF THE INVENTION

The invention also provides methods for alleviating cravings including those associated with addiction including cravings for sugars, carbohydrates, alcohol, nicotine, cocaine, amphetamine, opiate and non-opiate analgesics and the like by administration of an effective amount of nerve growth factor (NGF) or a subunit thereof and particularly the beta-subunit of NGF. Nerve growth factor is commercially available from suppliers such as Sigma. Particularly preferred is the use of recombinant produced beta-subunit of NGF which is available from Sigma and EMD Biosciences. The nerve growth factor is preferably administered in an amount ranging from about 0.001 to 10 microgram per day and is preferably formulated in a liquid vehicle and provided at a concentration of approximately 0.04 micrograms as a single drop. A single drop of nerve growth factor is within the range of 0.001 to 1 microgram. More preferably, a drop of nerve growth factor composition is in the amount of 0.02 micrograms per drop. The nerve growth factor composition is more preferably administered in an amount ranging from about 0.05 to 1 microgram per day or even more preferably administered in an amount ranging from about 0.01 to 0.1 micrograms per day. A preferred route of administration is sublingual, but other routes, such as bucal, oral drench, subcutaneous, intradermal, and intravenous, are expected to work.

The invention also provides a method of alleviating symptoms of a psychological condition selected from the group consisting of sleep disorders, chronic fatigue syndrome, tension headaches, and the physical discomfort of constipation that arise as a result of complications from a psychological condition by administering nerve growth factor to a patient in need thereof, wherein the nerve growth factor is in an amount ranging from 0.001 to 10 micrograms per day, and is preferably formulated in a liquid vehicle and provided at a concentration of approximately 0.04 micrograms as a single drop. A single drop of nerve growth factor is within the range of 0.001 to 1 microgram. More preferably, a drop of nerve growth factor composition is in the amount of 0.02 micrograms per drop. The nerve growth factor composition is more preferably administered in an amount ranging from about 0.05 to 1 microgram per day or even more preferably administered in an amount ranging from about 0.01 to 0.1 micrograms per day. A preferred route of administration is sublingual, but other routes, such as bucal, oral drench, subcutaneous, intradermal, and intravenous are expected to work.

The present invention provides methods for treating patients with symptoms of major depression by topically, sublingually, or subcutaneously administering a small amount of nerve growth factor. Methods of the invention are also useful for treating dysthymia including, but not limited to, treating the symptoms of distress and difficulty in performing everyday functions. Methods of the invention are also useful for treating depressed moods including, but not limited to, elderly depression and adolescent depression. In those cases, methods of the invention reduce feelings of sadness, gloominess, emptiness, fatigue, loss of appetite, body aches and pains, and sleeping difficulties.

The present invention also provides methods for treating patients with symptoms of bipolar disorders by topically, sublingually, or subcutaneously administering a small amount of nerve growth factor. Methods of the invention are also useful for treating type I bipolar disorder including, but not limited to, treating the manic symptoms such as elevated moods, hyperactivity, over-involvement in activities, inflated self-esteem, and little need of sleep and the depressed phase including loss of self-esteem, withdrawal, sadness, cold sweats, and risk of suicide. Disorders subject to therapeutic treatment using nerve growth factor include type II bipolar disorder and attention deficit disorder (ADD).

The present invention also provides methods for treating a variety of disorders that arise as a result of complications of depression or some other psychological condition such as bi-polar, disorder, anxiety disorders, panic attacks, agoraphobia, or attention deficit syndrome by topically, sublingually, or subcutaneously administering to humans a small amount of nerve growth factor. These methods are useful in treating symptoms associated with PMS, PMDD, various sleep disorders, chronic fatigue syndrome, tension headaches, and constipation. In those cases, methods of the invention reduce the feelings of depression, irritability, discomfort, fatigue, bloating, and cold sweats (night sweats).

The present invention also provides methods for treating various anxiety disorders by topically, sublingually, or subcutaneously administering to humans a small amount of nerve growth factor. These methods are also useful for treating panic disorders, and agoraphobia including, but not limited to, those involving shortness of breath, dizziness, palpitations, trembling, sweating, choking, nausea, chest pain, hot flashes or chills, fear of dying, fear of losing control, numbness, fear of going insane, feelings of detachment, feelings of helplessness, and avoidance of crowds, especially if escape or assistances is not immediately available.

The following Examples illustrate the methods of the invention with respect to treatment of psychological conditions, and, in particular, with respect to preferred methods of treating depression, anxiety disorders, and mid-cycle dysphoria. In particular, nerve growth factor was used to treat these various psychological disorders. The nerve growth factor is derived from snake venom, specifically *Vipeara lebotina* and was purchased from Sigma, Inc. or in other cases was a recombinantly produced beta-subunit fragment of NGF obtained from EMD Biosciences. Numerous improvements and further aspects of the invention are apparent to the skilled artisan upon consideration of the Examples, which follows.

The following Examples illustrate the methods of the invention with respect to treatment of various psychological conditions and in particular depression, various anxiety disorders, panic attacks, agoraphobia or bi-polar disorders. In addition, the Examples illustrate the methods of the invention with respect to treatment of various symptoms associated with PMS, PMDD, tension headaches, sleep disorders, constipation and cravings that arise as complications of the psychological conditions listed above. Numerous improvements and further aspects of the invention are apparent to the skilled artisan upon consideration of the Examples which follow.

Example I

A 51-year old female patient presented with a 15 year history of panic attacks and agoraphobia, was unable to perform everyday activities such as shopping, or other social functions. She began treatment with nerve growth factor at a rate and amount of one drop (0.04 µg/drop) per day by sublingual administration for approximately three weeks. Dosage frequency was decreased to an "as needed" basis, and such that the patient was being treated by administration of one drop (0.05 ml) (0.008 µg/drop) of NGF per month. During the first six months of treatment, she was increasingly able to perform everyday activities such as shopping, including weekly visits to the supermarket, attending church functions, and attending other civic events.

Example II

According to this example, a 59-year old female patient presented with a history of anxiety attacks. The subject was treated with sublingual administration of one drop (0.05 ml) (0.02 µg/drop) of NGF once a day. Patient's anxiety attacks subsided and her general mood improved. Patient has been on therapy for over six months.

Example III

A 42-year old female was diagnosed with anxiety, panic disorder, and hot flashes by her physician. She began treatment with NGF at a rate and an amount of one drop (0.05 ml) (0.04 µg/drop) per day by sublingual administration. After one week of treatment, her anxiety and panic episodes became less frequent and her general mood improved, but her hot flashes persisted. The dosage of NGF increased to a rate and amount of two drops (0.05 ml) (0.04 µg/drop) wherein patient experienced even less anxiety, panic episodes and hot flashes.

Example IV

A 78-year old female, who suffered from both depression and anxiety, was treated with a dose of 1 drop (0.05 ml) (0.02 µg/drop) per day of NGF by sublingual administration. After thirty days of treatment, her depression symptoms subsided after NGF administration began, but she exhibited less improvement on her anxiety. Treatment of the patient continues.

Example V

A 61-year old female, who suffered from clinical depression, as diagnosed by her physician (Beck score of 20; Hamilton score of 19), was initially placed on complex medicine regimen developed in applicants' lab for treatment of strokes. Nerve growth factor is one of the components of this medical regimen. Patient experienced less depression after this treatment, but the depression returned after 4 weeks. The complex treatment was suspended. In its place, nerve growth factor alone was administered at a dose of one drop (0.05 ml) (0.04 µg/drop) per day by sublingual administration. After two weeks of treatment, patient's depression decreased as indicated by a Beck score of 13 and a Hamilton score of 6. In addition, patient noticed a decreased level of constipation in comparison to prior levels of constipation suffered before NGF treatment.

Example VI

A 47-year old female, who suffered from clinical depression and anxiety, was treated by administration of a dose of one drop (0.05 ml) (0.04 µg/drop) of nerve growth factor per day by sublingual administration. After two weeks of treatment, the patient's emotional state improved, but her fatigue remained unchanged. Patient continues to be treated.

Example VII

A 48-year old female presented with a diagnosis of depression, irritability, frequent headaches, restless sleep, and hot flashes during her one-week premenstrual cycle. The patient also complained of chronic month long anxiety. The patient was administered NGF at a dose of one drop (0.05 ml) (0.02 µg/drop) per day by sublingual administration for 90 days. Upon patient's first menstrual cycle after starting NGF treatments (about one month), she was re-diagnosed. Under the NGF treatments, she had experienced less irritability and depression during her premenstrual cycle. In addition, patient's sleep improved, she experienced no headaches, and her hot flashes disappeared. Finally, her chronic month-long anxiety improved. Patient now continues use of NGF as needed.

Example VIII

A 50-year old female diagnosed with severe situational anxiety and depression following the suicide of one of the patient's clients. She was treated by administration of NGF at a dose of one drop (0.05 ml) (0.02 µg/drop) per day by sublingual administration for two months. The NGF treatment provided some relief to her anxiety.

Example IX

A 50-year old female, who suffered from depression and anxiety, as diagnosed by her physician, had previously been treated with Paxil and more recently, Prozac and Xanax. Prozac treatment was discontinued and, at this time, the patient exhibited a Beck inventory score of 26. Patient was placed on a dose of 1 drop (0.05 ml) (0.02 μg/drop) per day of NGF by sublingual administration. After two weeks of treatment with NGF, patient showed improvement in her mood and anxiety scoring a Beck inventory score of only 11. NGF treatment continues with patient showing less dependency of Xanax medication (decrease from one/day to ¾ pill/day).

Example X

A 50-year old female patient suffering from multiple sclerosis participated in NGF treatments. This patient also suffered a life-long history of constipation that is exaggerated as a consequence of being wheelchair-bound. Without treatment with nerve growth factor, she has one bowel movement every 7-10 days. With NGF treatment at a dose of one drop (0.05 ml) (0.02 μg/drop) per day by sublingual administration, the patient experienced one bowel movement every day.

Example XI

A female patient suffering from hot flashes and mid cycle dysphoria, as diagnosed by her physician, was placed on a dose of 2 drops (0.05 ml/drop) (0.02 μg/drop) of NGF 2-3 times a night by sublingual administration. Subsequently, patient's daytime hot flashes occurred half as often as before NGF treatment, and the hot flashes were less severe. Her sadness and weeping episodes also disappeared due to the treatment. Overall, she was doing well emotionally after two weeks of treatment.

Example XII

A 48-year old female, with a history of chronic constipation since early childhood, began NGF therapy at the rate of one drop of NGF (0.05 ml/drop; 0.02 μg/drop) sublingually twice daily. No response was seen in one week so the dosage increased to one drop of NGF (0.05 ml/drop; 0.02 μg/drop) sublingually three times daily. After two days of the increased dosage protocol the subject experienced normal bowel activity without the assistance of an enema or laxative for the first time in years. The subject continued with the three drops of NGF (0.05 ml/drop; 0.02 μg/drop) sublingually per day regimen for two weeks, then began decreasing the frequency of administration, first to one drop of NGF twice daily, then to one drop per day, and then on an as needed basis. The subject now reports daily bowl movements without the need for any medication, including NGF. No adverse reaction (e.g., including loss of bowel control) to the NGF therapy was observed in the subject.

Example XIII

A six-month old male with daily constipation was started at one drop of NGF (0.05 ml/drop; 0.02 μg/drop) sublingually once daily. After four days the subject was no longer constipated (even without a change in diet). After about three weeks of the daily NGF therapy the subject no longer needed the daily drop and was weaned off over a two week period. No adverse reaction (e.g., including loss of bowel control) to the NGF therapy was observed in the subject.

Example XIV

A 63-year old woman with a forty year history of multiple sclerosis and chronic constipation found relief using NGF at one drop (0.05 ml/drop; 0.02 μg/drop) sublingually twice daily for a month. The subject now continues using one drop of NGF (0.05 ml/drop; 0.02 μg/drop) daily or every other day to maintain the improved status that the subject had experienced for over a year. No adverse reaction (e.g., including loss of bowel control) to the NGF therapy was observed in the subject.

Example XV

An 88-year old woman with chronic constipation over a period described by the subject as "forever" was started on NGF therapy at one drop (0.05 ml/drop; 0.02 μg/drop) sublingually twice daily. Relief was reported within three days. Now a drop (0.05 ml/drop; 0.02 μg/drop) of NGF is taken as needed. No adverse reaction (e.g., including loss of bowel control) to the NGF therapy was observed in the patient.

Example XVI

Several older dogs and cats have also been successfully treated for constipation with one drop of NGF (0.05 ml/drop; 0.02 μg/drop) sublingually or by subcutaneous injection once or twice daily as in the human subjects set forth in Examples XII-XV. No adverse reaction (e.g., including loss of bowel control) to the NGF therapy was observed in the patients.

Example XVII

An 84 year old practicing physician with a craving for sweets was treated with NGF therapy with one drop of recombinant produced human NGF beta-subunit (EMD Biosciences) (0.05 ml/drop; 0.02 μg/drop) administered sublingually three times per day. After five days he noticed a decrease in his craving, and after two weeks it had completely ceased. He discontinued NGF therapy and after three weeks still had limited or no craving. Of interest was his observation that he also decreased his coffee intake, even though that was not the target of the exercise. He was happy with both outcomes. There were no adverse events.

Example XVIII

A 73 year old male with a long-standing craving for ethanol began NGF therapy with one drop of recombinant produced human NGF beta-subunit (EMD Biosciences) (0.05 ml/drop; 0.02 μg/drop) administered sublingually three times daily. He noticed that within the first two or three days his desire for a pre-dinner drink was decreased. With continued use he was able to decrease the frequency of NGF drop administration without loss of benefit. After nearly one year of NGF treatment he occasionally takes a social drink but has no cravings of the sort previously noted.

Example XIX

A female confirmed alcoholic in her mid-40s began NGF therapy by administering one drop of recombinant produced human NGF beta-subunit (EMD Biosciences) (0.05 ml/drop; 0.02 μg/drop) administered sublingually twice daily. She noted that if she complied with that regimen she was able to avoid drinking with minimal effort. However, if she missed the second drop in the late afternoon she would begin drinking alcohol in the evening. She tried taking two drops in the morning and found she was able to decrease or eliminate her craving all day without an afternoon dose.

Example XX

A nurse with an addiction to prescription analgesics sought help in recognition of her problem which had not resolved with conventional therapy. After one week of sublingually administering one drop of recombinant produced human NGF beta-subunit (EMD Biosciences) (0.05 ml/drop; 0.02 μg/drop) twice daily she was aware of a significant decrease in craving within four days, and after two weeks had none at all. She has remained craving-free for more than one year.

Example XXI

A 61 year old female with an alcohol craving began taking NGF drops at the rate of one drop of recombinant produced human NGF beta-subunit (EMD Biosciences) (0.05 ml/drop; 0.02 μg/drop) administered sublingually twice daily and within one week noticed a dramatic decrease in her desire for alcohol. She continued at that rate for about six weeks, with no craving. Within two weeks of discontinuing the drops she began taking a drink or two each evening, noticed her craving, and again initiated NGF therapy. Her craving for alcohol decreased with the reinitiation of NGF therapy but increased again when she again stopped taking the NGF drops.

Example XXII

Several patients have used NGF drops as described herein to counter their craving for food and in an effort to lose weight. Results have varied from little progress to significant weight loss. Compliance has been reported as a real problem for those who experienced no decrease in body weight.

Example XXIII

NGF administration was tested in a validated animal model (P rats) for alcohol consumption and showed that recombinant produced human NGF beta-subunit (EMD Biosciences) at a doses of either one drop (0.05 ml/drop; 0.02 μg/drop) or two drops administered sublingually resulted in a statistically significant decrease in ethanol consumption as early as two hours after the first dose.

Numerous modifications and variations in the practice of the invention are expected to occur to those skilled in the art upon consideration of the presently preferred embodiments thereof. Consequently, the only limitations which should be placed upon the scope of the invention are those which appear in the appended claims.

What is claim is:

1. A method of reducing cravings comprising administering to a subject in need thereof nerve growth factor in an amount effective to reduce the craving wherein the reduction of the craving is monitored and the craving is selected from the group consisting of cravings for sugars, carbohydrates, alcohol, nicotine, cocaine, amphetamine, opiate and non-opiate analgesics.

2. The method of claim 1, wherein said nerve growth factor is administered by a mode selected from the group consisting of sublingual, bucal, oral drench, subcutaneous, intradermal, or intravenous.

3. The method of claim 2, wherein said nerve growth factor is administered sublingually.

4. The method of claim 1, wherein said nerve growth factor is administered at a daily dosage of from 0.001 to 1 microgram per day.

5. The method of claim 1, wherein said nerve growth factor is administered at a daily dosage of from 0.01 to 0.1 microgram per day.

6. The method of claim 1 wherein the nerve growth factor is a beta-subunit of nerve growth factor.

* * * * *